(12) United States Patent
Krimsky et al.

(10) Patent No.: US 10,417,383 B2
(45) Date of Patent: Sep. 17, 2019

(54) REMOTE MEDICAL EVALUATION

(71) Applicant: Specialist On Call, Inc., Reston, VA (US)

(72) Inventors: William Sanford Krimsky, Bel Air, MD (US); Stephen Robert Selinger, Baltimore, MD (US); Alexander Marc Nason, Potomac, MD (US); Carrie Christine Castellon, Swansboro, NC (US)

(73) Assignee: SPECIALISTS ON CALL, INC., Reston, VA (US)

( * ) Notice: Subject to any disclaimer, the term of this patent is extended or adjusted under 35 U.S.C. 154(b) by 662 days.

(21) Appl. No.: 14/814,254

(22) Filed: Jul. 30, 2015

(65) Prior Publication Data

US 2016/0034657 A1 Feb. 4, 2016

Related U.S. Application Data

(60) Provisional application No. 62/031,714, filed on Jul. 31, 2014.

(51) Int. Cl.
*G06F 19/00* (2018.01)
*G06Q 10/10* (2012.01)

(52) U.S. Cl.
CPC ..... *G06F 19/3418* (2013.01); *G06Q 10/1095* (2013.01)

(58) Field of Classification Search
None
See application file for complete search history.

(56) References Cited

U.S. PATENT DOCUMENTS

2005/0251415 A1* 11/2005 Pak ..................... G06F 19/3418
705/2
2006/0095429 A1 5/2006 Abhyankar et al.
(Continued)

FOREIGN PATENT DOCUMENTS

| CN | 1495635 | 5/2004 |
| CN | 1930572 | 3/2007 |
| CN | 102945538 | 2/2013 |

OTHER PUBLICATIONS

International Search Report issued in PCT/2015/042905 dated Nov. 2, 2015.
(Continued)

*Primary Examiner* — Michael Tomaszewski
(74) *Attorney, Agent, or Firm* — DLA Piper LLP US (57) ABSTRACT

A consult coordination center (CCC) computer may comprise a database and a processor. A scheduling module executed by the processor may schedule a patient assessment session for a facility, the patient assessment session comprising an assessment of at least one patient in the facility by a remote health care professional to determine whether the at least one patient should be given more immediate care. An assignment module executed by the processor may assign the scheduled patient assessment session to a health care professional computer. A connection module executed by the processor may create a remote connection between the health care professional computer and a computer at the facility via a network to facilitate the patient assessment session, the remote connection comprising a video feed from the computer at the facility to the health care professional computer. A data module executed by the processor may retrieve a report of a previous patient assessment session at the facility from the database, send the report of the previous patient assessment session at the facility to the health care professional computer, receive a
(Continued)

report of the patient assessment session, and store the report of the patient assessment session in the database.

30 Claims, 10 Drawing Sheets

(56) References Cited

U.S. PATENT DOCUMENTS

| | | | |
|---|---|---|---|
| 2008/0140160 A1* | 6/2008 | Goetz | A61N 1/37288 607/60 |
| 2011/0040569 A1 | 2/2011 | Schoenberg | |
| 2011/0166465 A1 | 7/2011 | Clements et al. | |
| 2013/0060576 A1* | 3/2013 | Hamm | G06F 19/3418 705/2 |
| 2013/0271556 A1* | 10/2013 | Ross | G06F 19/3418 348/14.07 |
| 2014/0019149 A1 | 1/2014 | Yu et al. | |

OTHER PUBLICATIONS

Written Opinion issued in PCT/2015/042905 dated Nov. 2, 2015.
CN Office Action dated Nov. 19, 2018 in Application No. 201580041464.X.

* cited by examiner

CRITICAL CARE SMART SHEET
                                                                                400

1. General orienting sentence on the patient (e.g. 62 yo man admitted for pneumonia):

2. Identify Chief Physiologic Deterioration (See FIG. 4B)

3. Process Metrics Evaluation:
    a. Are there any devices in place (lines, tubes, etc.)? Y/N         • If YES - are any or all of them still necessary Y/N     b. Has this patient reached their nutritional goal? Y/N         • If NO - has this been addressed with patient's attending? Y/N     c. Are there current issues with pain management in this patient? Y/N         • If YES - have these been addressed? Y/N     d. Is skin integrity intact? Y/N         • If NO - is this being addressed? Y/N     e. Are there issues with delirium? Y/N         • If YES - are these being addressed? Y/N     f. Is this patient on appropriate prophylaxis (VTE, SUP, VAP, etc.)? Y/N         •If NO - are these being addressed Y/N     g. Has the patient been mobilized Y/N     h. Are there ethical or care philosophy or family issues Y/N

4. Do you or your patient need help? – If yes, then SOC SMART Doctor will coordinate a consult for the patient.

FIG. 4A

Physiological Deterioration (note not all inclusive)

- A step change in systolic BP by 40 mm

- A systolic BP < 90 mm

- A MAP < 60 mm

- Heart rate of 120 or greater

- An abrupt change in metal status

- A change in perfusion (i.e. decreased UO, mottling, escalating lactate)

- An increase in FiO2 required by 30%

- An increase in RR to 28 or greater

SMART Sign-out

Patient Name: _______________________________ DOB: _________
Hospital: _________________________________
City, State: _______________________________

1. General orienting sentence on the patient (e.g., 62 yo man admitted for phneumonia):

2. Identify Chief Physiologic Deterioration (see below)

3. Process Metrics Evaluation:
    a. Are there any devices in place (lines, tubes, etc.)? Yes   No     b. Has this patient reached their nutritional goal? Yes   No     c. Are there current issues with pain management in this patient? Yes   No     d. Is skin integrity intact? Yes   No     e. Are there issues with delirium? Yes   No     f. Is this patient on appropriate prophylaxis (VTE, SUP, VAP, etc.)? Yes   No     g. Has the patient been mobilized Yes   No     h. Are there ethical or care philosophy or family issues Yes   No

4. List the key/critical issues

5. Status change in the past 24 hours?           Yes        No

Physiological Deterioration (note not all inclusive)

| | |
|---|---|
| A step change in systolic BP by 40 mm | An abrupt change in metal status |
| A systolic BP < 90 mm | A change in perfusion (i.e. decreased UO, mottling, escalating lactate) |
| A MAP < 60 mm | An increase in FiO2 required by 30% |
| Heart rate of 120 or greater | An increase in RR to 28 or greater |

FIG. 9

REMOTE MEDICAL EVALUATION

CROSS REFERENCE TO RELATED APPLICATIONS

This application is based on and derives the benefit of U.S. Provisional Patent Application No. 62/031,714, filed on Jul. 31, 2014. The entirety of the above-listed Applications is incorporated herein by reference.

DETAILED DESCRIPTION OF SEVERAL EMBODIMENTS

Systems and methods described herein may provide remote safety management and recommended triage evaluations for patients in intensive care units (ICUs) or other clinical areas. A remote evaluation session may include performing an assessment for each patient in an ICU by a remote doctor or other health care professional (e.g., nurse, assistant technician, etc., hereinafter collectively referred to as "doctor"), and generating records related to the assessments. The remote evaluation may proactively identify patients in need and assess the ongoing integrity of care. The remote evaluation may include regular (e.g., daily) patient assessment coordinated between remote and on-site personnel which may enable a brief "eyes-on" daily patient assessment, ensure process integrity, and assess common failure modes with respect to the disciplinary work that should be done on every patient. The remote evaluation may also establish a bi-directional channel to ask for and/or to provide further help. If it is established that further help is required, then the patient may be channeled into a different level of care for a one-to-one evaluation.

Systems and methods described herein may comprise one or more computers, which may also be referred to as processors. A computer may be any programmable machine or machines capable of performing arithmetic and/or logical operations. In some embodiments, computers may comprise processors, memories, data storage devices, and/or other commonly known or novel components. These components may be connected physically or through network or wireless links. Computers may also comprise software which may direct the operations of the aforementioned components. Computers may be referred to with terms that are commonly used by those of ordinary skill in the relevant arts, such as servers, PCs, mobile devices, routers, switches, data centers, distributed computers, and other terms. Computers may facilitate communications between users and/or other computers, may provide databases, may perform analysis and/or transformation of data, and/or may perform other functions. It will be understood by those of ordinary skill that those terms used herein are interchangeable, and any computer capable of performing the described functions may be used.

Computers may be linked to one another via a network or networks. A network may be any plurality of completely or partially interconnected computers wherein some or all of the computers are able to communicate with one another. It will be understood by those of ordinary skill that connections between computers may be wired in some cases (e.g., via Ethernet, coaxial, optical, or other wired connection) or may be wireless (e.g., via Wi-Fi, WiMax, or other wireless connection). Connections between computers may use any protocols, including connection oriented protocols such as TCP or connectionless protocols such as UDP. Any connection through which at least two computers may exchange data can be the basis of a network.

Figure 1:
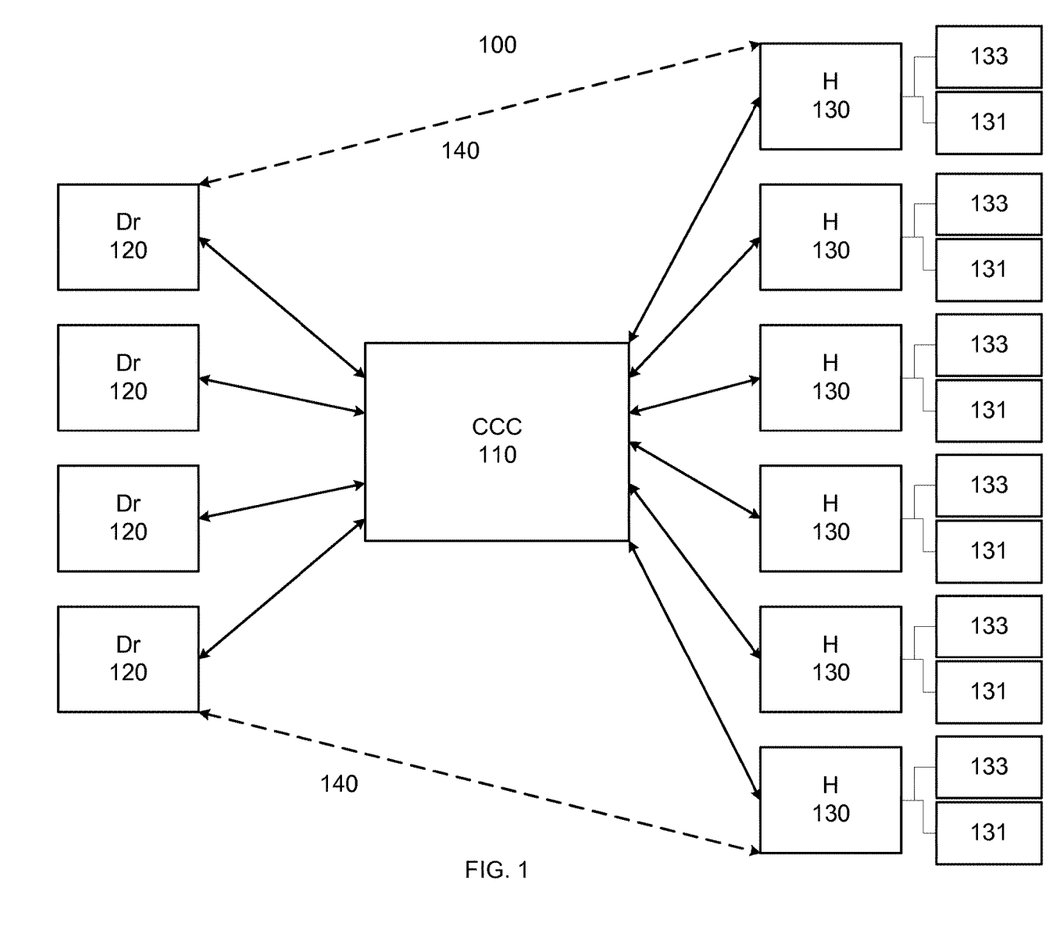
FIG. 1 is a schematic diagram of a network according to an embodiment of the invention.

FIG. 1 is a network 100 according to an embodiment of the invention. The network 100 may include a consult coordination center (CCC) 110 comprising one or more computers in communication with one or more doctor computers 120 and one or more hospitals 130 (e.g., via one or more camera units 131 or other computers 133 at each hospital 130). Doctors and hospitals are shown in this example, although other specialists 120 and facilities 130 may be present in the network 100. For example, the system may be employed in nursing homes, long term acute care facilities and patient homes, among others. The CCC 110 may communicate with doctor computers 120 and hospital 130 computers via any network, such as the Internet. The CCC 110 may also include a call center which may be staffed to handle troubleshooting and/or other calls from doctors and/or hospitals 130. A remote evaluation session may be initiated for a hospital 130, for example at a time scheduled at the CCC 110. The remote evaluation sessions are described in greater detail below, but may generally include remote doctor/patient interaction via a doctor computer 120 and one or more systems at the hospital 130. The CCC 110 may indicate to the one or more doctor computers 120 that the hospital 130 is ready for the remote evaluation session, and a doctor at one of the doctor computers 120 may accept the remote evaluation assignment and begin the remote evaluation session. The CCC 110 may facilitate a direct connection between the doctor computer 120 (and doctor) and the hospital 130 computer. After completion of the remote evaluation session, the hospital 130 or doctor computer 120 may send records generated during the session to the CCC 110, so that they may be used in future sessions. Thus, the CCC 110 may serve as a communications hub for the doctor computers 120 and the hospitals 130 and as a data repository for medical records useful to both the doctors and hospital 130 personnel.

Figure 6:
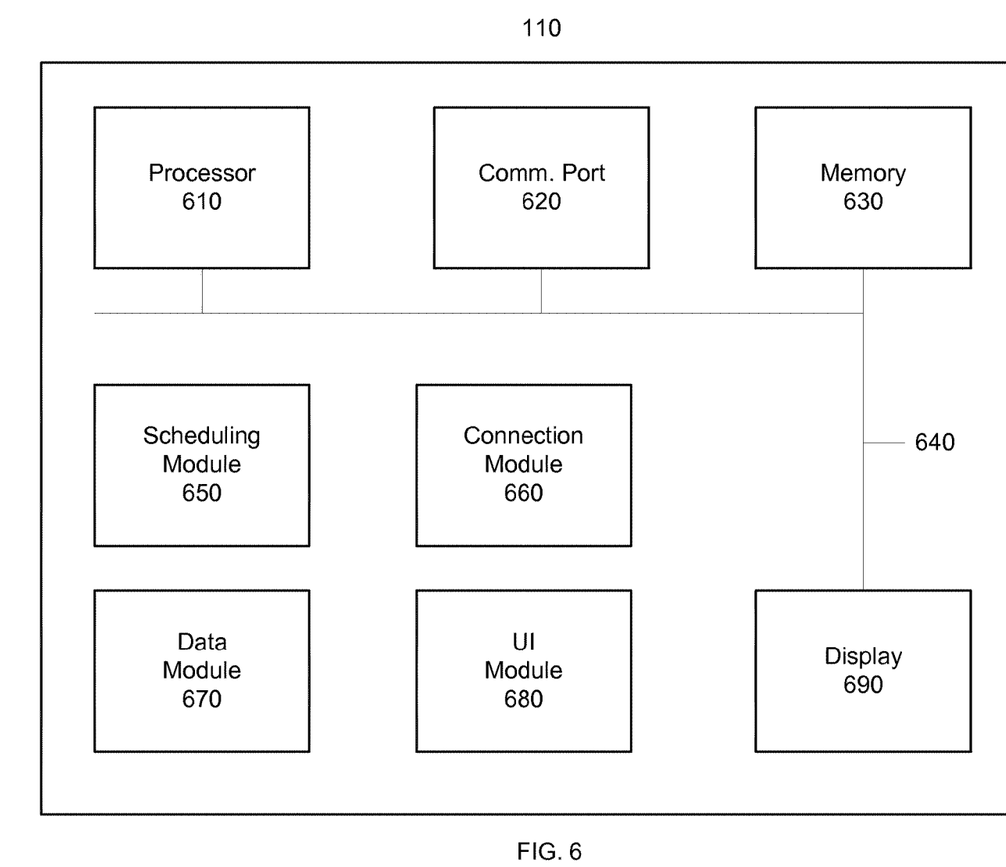
FIG. 6 is a schematic block diagram of a consult coordination center according to an embodiment of the invention.

FIG. 6 is a CCC 110 according to an embodiment of the invention. The CCC 110 may include one or more computers. The one or more computers may include a processor 610, a communication port 620 which may be configured to connect to the network 100, a memory 630, a display 690, and/or other hardware, which may be interconnected by a bus 640. The one or more computers may include a scheduling module 650, a connection module 660, a data module 670, a user interface (UI) module 680, and/or other modules. Such modules may be software stored in memory 630 and executed on processor 610. Example functions of these modules are described in greater detail below.

FIG. 1 depicts an embodiment of a CCC 110 that is central to a plurality of doctor computers 120 and hospitals 130, but in some embodiments the CCC 110 may be distributed. For example, a geographic region may have several hospitals 130. One of the hospitals 130 in the region may serve as a hub for the remaining hospitals 130 in the region. The hub hospital 130 may include a CCC 110 or elements of a CCC 110. Thus, for example, the hub hospital 130 could perform some or all of the scheduling, communications, data collection, etc. for the regional hospitals 130. The hub hospital 130 may also have remote evaluations performed on its own patients. The hub hospital 130 may include an entire CCC 110, or may be in communication with another CCC 110 as shown in FIG. 1.

Figure 7:
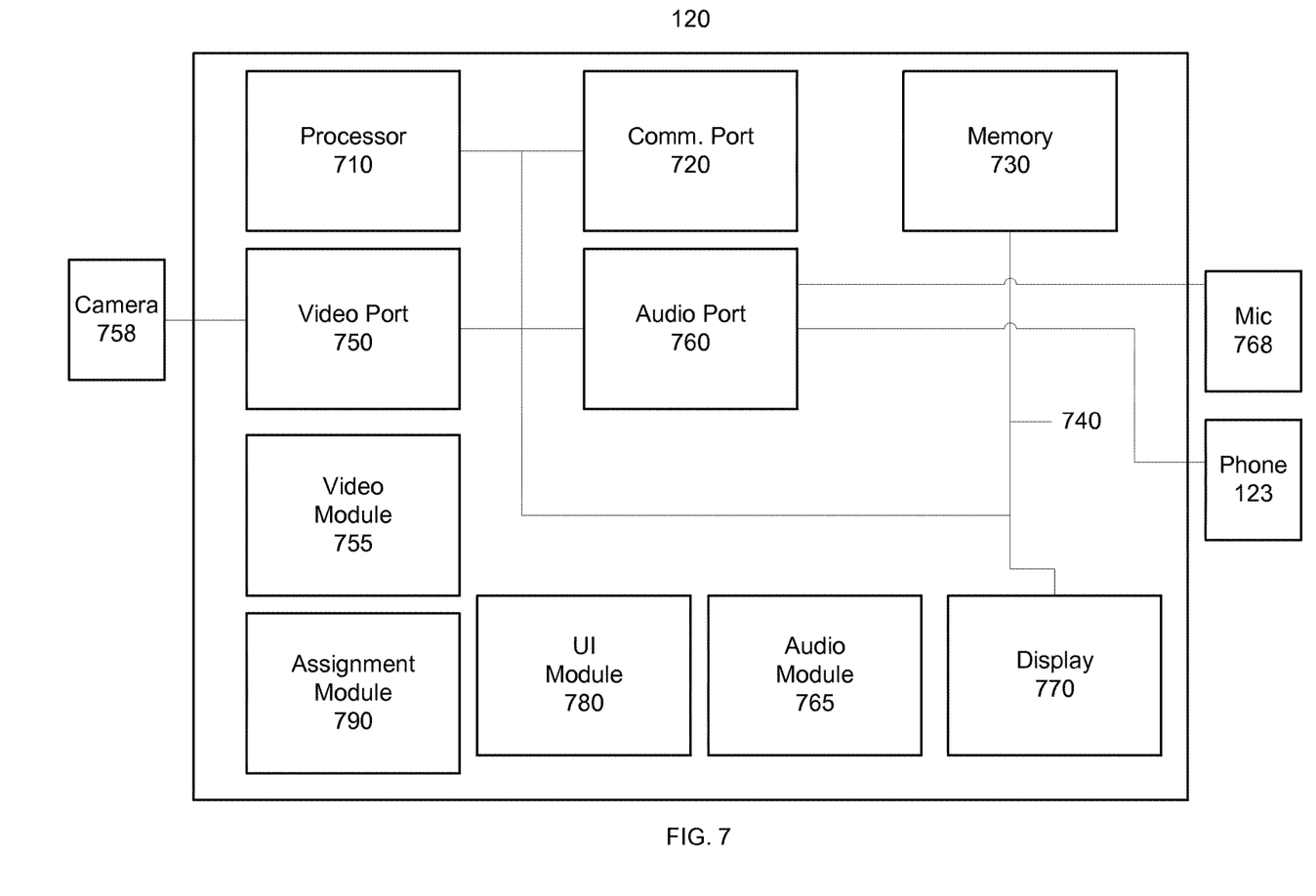
FIG. 7 is a schematic block diagram of a doctor computer according to an embodiment of the invention.

FIG. 7 is a doctor computer 120 according to an embodiment of the invention. The doctor computer 120 may include one or more computers. The one or more computers may include a processor 710, a communication port 720 which may be configured to connect to the network 100, a memory 730, a video port 750 to which a camera 758 may be connected, an audio port 760 to which a microphone 768 may be connected, a display 770, and/or other hardware, which may be interconnected by a bus 740. The ports may be any ports capable of exchanging data (e.g., Ethernet, USB, etc.). The one or more computers may include a video module 755, an audio module 765, a UI module 780, an assignment module 790, and/or other modules. Such modules may be software stored in memory 730 and executed on processor 710. Example functions of these modules are described in greater detail below. A phone 123 may be part of the doctor computer 120 (e.g., connected via the audio port 760) or may be separate from the doctor computer 120.

Figure 8:
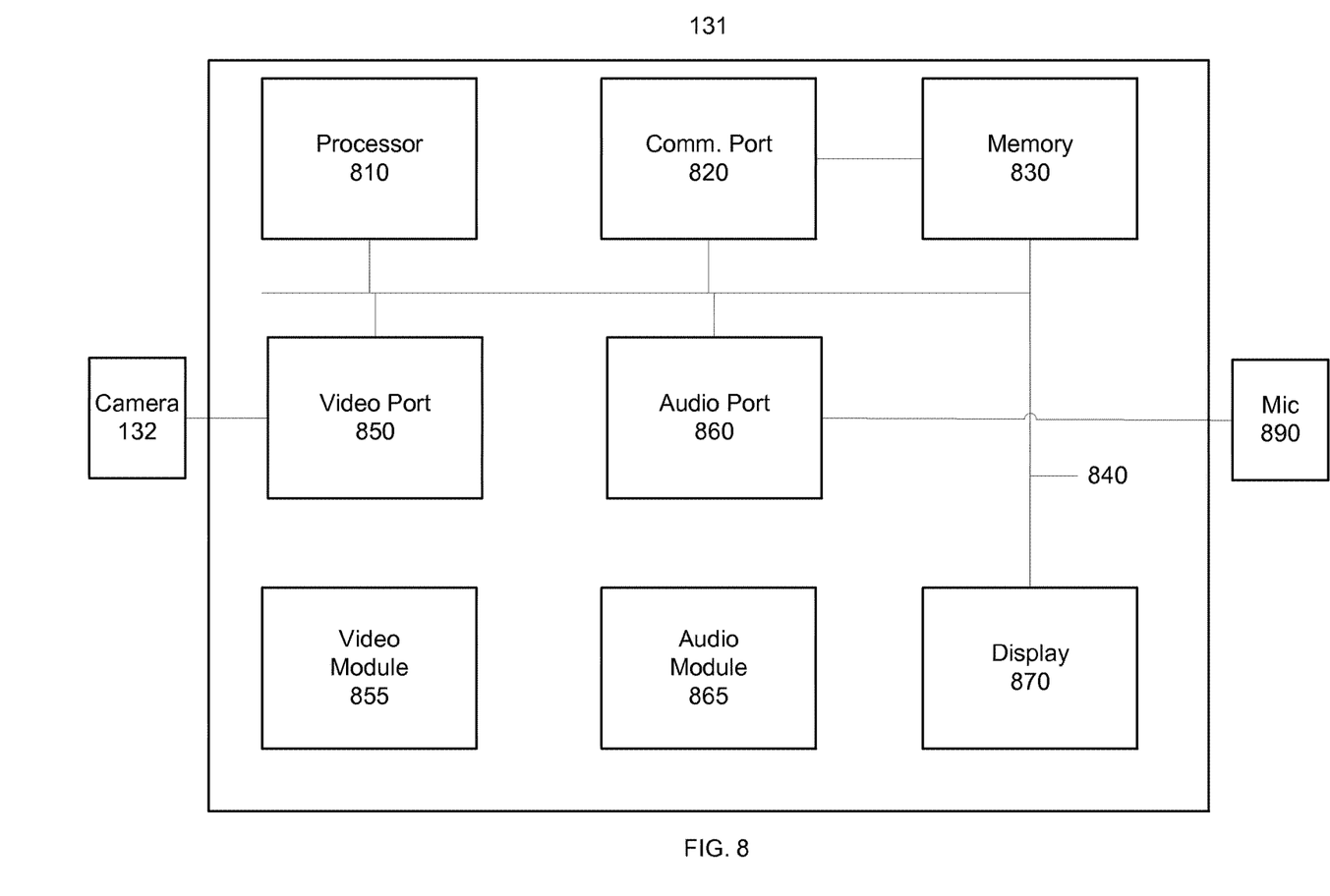
FIG. 8 is a schematic block diagram of a camera unit according to an embodiment of the invention.

FIG. 8 is a camera unit 131 according to an embodiment of the invention. The camera unit 131 may be housed in a portable device that may be brought around to various patients in the hospital 130. For example, the camera unit 131 may be housed in a wheeled cart or a self-propelled robotic unit. The camera unit 131 may include one or more computers. The one or more computers may include a processor 810, a communication port 820 which may be configured to connect to the network 100, a memory 830, a video port 850 to which a camera 132 may be connected, an audio port 860 to which a microphone 890 may be connected, a display 870, and/or other hardware, which may be interconnected by a bus 840. The ports may be any ports capable of exchanging data (e.g., Ethernet, USB, etc.). The one or more computers may include a video module 855, an audio module 865, a UI module 880, and/or other modules. Such modules may be software stored in memory 830 and executed on processor 810. Example functions of these modules are described in greater detail below.

Figure 2:
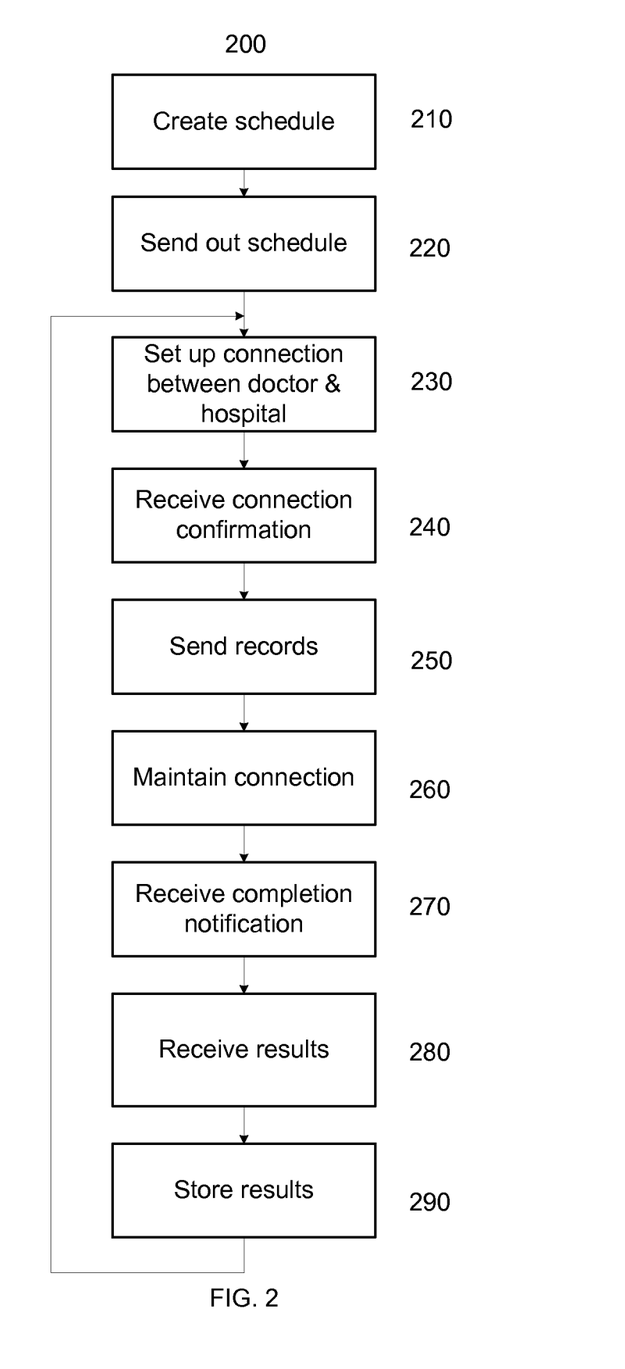
FIG. 2 is a flowchart of a session management process according to an embodiment of the invention.

FIG. 2 is a session management process 200 according to an embodiment of the invention. This process 200 may be performed by the CCC 110 to establish, maintain, and process remote evaluation sessions. Multiple hospitals 130 may request remote evaluation services from the CCC 110. These hospitals 130 may be geographically spread out (e.g., in different time zones) and may operate on different schedules. The CCC 110 scheduling module 650 may create a schedule 210 indicating when each hospital 130 is ready for remote evaluation. The schedule may include a start time for a particular remote evaluation in each hospital 130. The schedule may take into account a number of patients in an ICU and an estimated time for evaluation per patient to create an approximate duration for each hospital's 130 session. The CCC 110 may distribute this schedule 220 to doctor computers 120 connected to the CCC 110 via the network 100. The UI module 780 of a doctor computer 120 may cause the display 770 to show the schedule to the doctor, and the doctor may indicate that he or she is ready to perform a remote evaluation session via interaction with the UI module 780 using any input device. The doctor may be able to select a specific hospital 130 from among several hospitals 130 that are ready for remote evaluation. For example, if a doctor has previously performed remote evaluations at a specific hospital 130, he or she may wish to perform subsequent sessions. However, the same doctor need not necessarily perform sessions with the same hospital 130 every time. The CCC 110 may also automatically assign doctors to hospitals 130 based on the schedule (e.g., if hospital X is estimated to take 1 hour beginning at midnight, and doctor Y is not otherwise assigned in the midnight to 1 AM time slot, doctor Y may be assigned to hospital X by the CCC 110).

Figure 5:
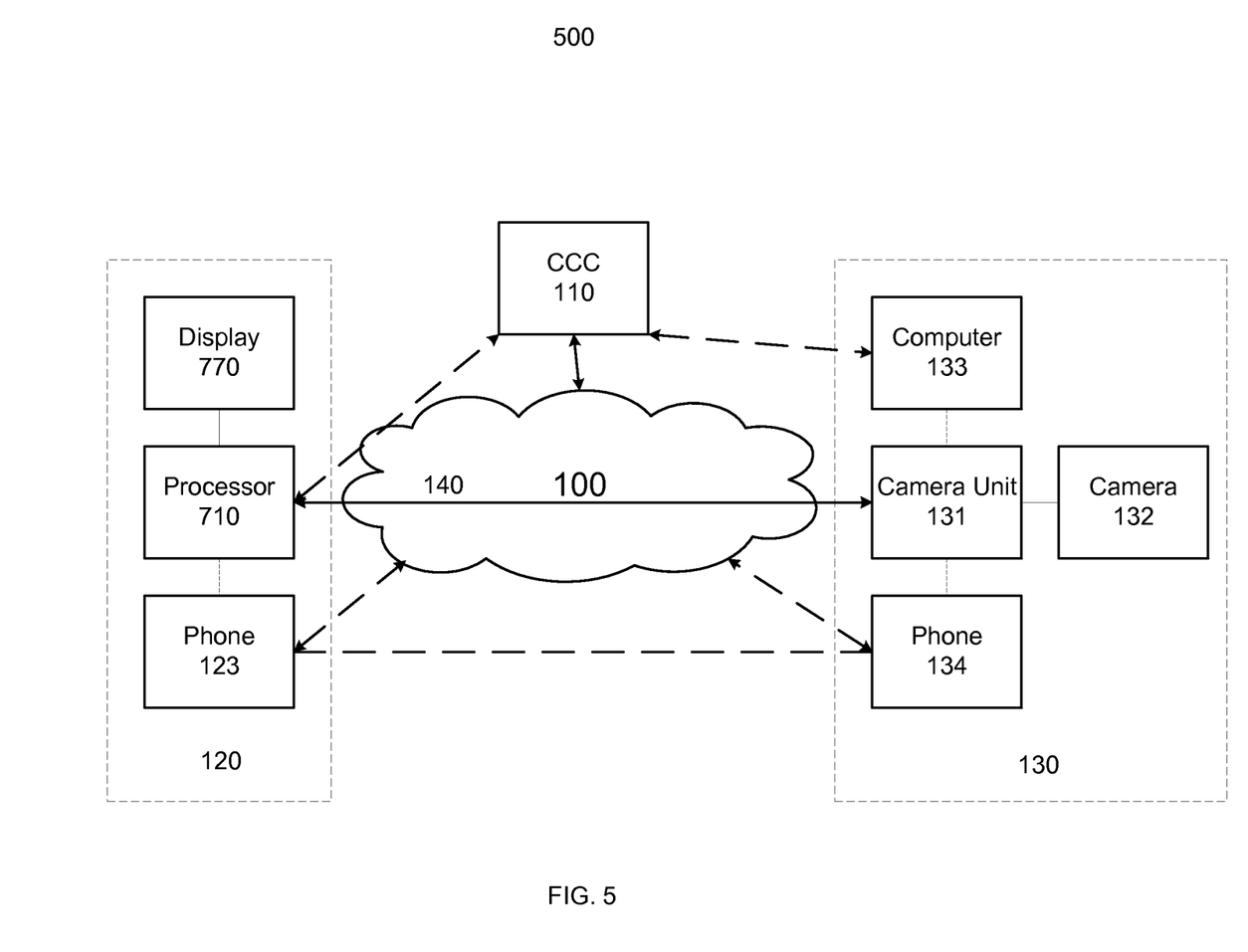
FIG. 5 is a schematic connection diagram according to an embodiment of the invention.

The doctor computer 120 may indicate the doctor's readiness at the start time for a hospital 130 and/or hospital 130 selection to the CCC 110, and the CCC 110 connection module 660 may set up a connection 230 between the doctor computer 120 and the hospital 130. FIG. 5 is a connection diagram 500 according to an embodiment of the invention. The hospital 130 may be equipped with a camera unit 131, as discussed above. The camera unit 131 may include a camera 132, and the camera unit 131 may capture video via the video port 850 and transmit the video to the doctor computer 120 via the communications port 820. Similarly, the camera unit 131 may capture audio via the audio port 860 and microphone 890 and transmit the audio to the doctor computer 120 via the communications port 820. The doctor computer 120 and camera unit 131 may be connected via the network 100 so that the doctor computer 120 may display images and/or video from the camera 132 on the display 770. Creating the connection may include establishing a connection with the connection module 660 of the CCC 110 and then handing off the connection so that the doctor computer 120 and camera unit 131 interact directly with one another via the network 100, without sending data through the CCC 110 after the handoff. The respective microphones 768, 890 and audio ports 760, 860 and/or the phone 123 may be used to establish an audio link between the doctor at the doctor computer 120 and individuals on site at the hospital 130, such as a nurse and/or patient, via the network 100. The connection between the doctor computer 120 and the camera unit 131 at the hospital 130 may be maintained through the CCC 110 (e.g., data may pass through the CCC 110) or through an independent network 100 connection (e.g., connection 140). The connection module 660 may monitor integrity of the connection during the session and may reestablish the connection if it breaks. The CCC 110 may facilitate additional communication, for example by providing a phone number for the hospital 130 to the doctor computer 120 and/or by providing a phone number for the doctor to the hospital 130. The hospital 130 may also include a phone 134 (e.g., an IP phone) which may be part of the camera unit 131 or separate from the camera unit 131. Thus, a doctor and a nurse could speak by phone in addition to interacting via the doctor computer 120 and camera unit 131, for example. The hospital 130 may also include additional computers 133, which may be used for interacting with the CCC 110, for example for data entry as described in greater detail below.

Returning to FIG. 2, once the connection is established, the connection module 660 of the CCC 110 may receive connection confirmation 240 from the doctor computer 120 and/or hospital 130. The data module 670 of the CCC 110 may send any medical records 250 that may be relevant to the remote evaluation session to the doctor computer 120. For example, records generated during prior remote evaluation sessions for the hospital 130 may be sent. If the remote evaluation session is for an ICU including multiple patients, the records may include information about each patient in the ICU gathered during the previous remote evaluation sessions. The CCC 110 may monitor and maintain the connection 260, for example by monitoring connection integrity and providing for reconnection if communication is broken. The doctor and hospital 130 personnel may perform the remote evaluation, and when the session is complete, the doctor computer 120 and/or hospital 130 may end the session. The CCC 110 may receive notification of session completion 270. The data module 670 of the CCC 110 may receive results of the remote evaluation session 280 from the doctor computer 120 and/or hospital 130 (e.g., via the hospital computer 133 or camera unit 131). For example, a doctor may proceed through a series of questions and perform a basic evaluation of patients in the ICU. The basic evaluation may include a visual evaluation of the patient facilitated by the video link between the camera 132 and doctor computer 120 display 770. Answers to the questions may be sent to the CCC 110. Example questions and specific evaluations are described in greater detail below. The results may also include an indication that a particular patient needs more specialized help. The CCC 110 may be able to refer the patient to more specialized help from a remote specialist, as discussed in greater detail below. The results may be entered into the doctor computer 120 via the UI and sent to the CCC 110, entered into a hospital 130 computer and sent to the CCC 110, and/or sent to the CCC 110 in some other way (e.g., faxed or phoned in) and entered into the CCC 110 on site. The CCC 110 may store the received results 290, and the results may be available for subsequent remote evaluation sessions at the hospital 130. After a remote evaluation session is completed, a doctor may move on to another hospital 130 for another session, and the process described above may be repeated. The CCC 110 may be able to perform session management 200 for multiple doctor computer 120 and hospital 130 connections at a time.

A remote evaluation session may include pointing a camera at a patient and making a brief general statement about the patient, identifying chief physiologic failure mode(s) for the patient, a doctor asking and hospital staff answering binary questions with respect to certain types of work that may be assessed on a daily basis (e.g., appropriate prophylaxis, nutrition, device management, etc.), and providing an opportunity for the hospital staff to solicit help and/or for the doctor to offer help.

Figure 3:
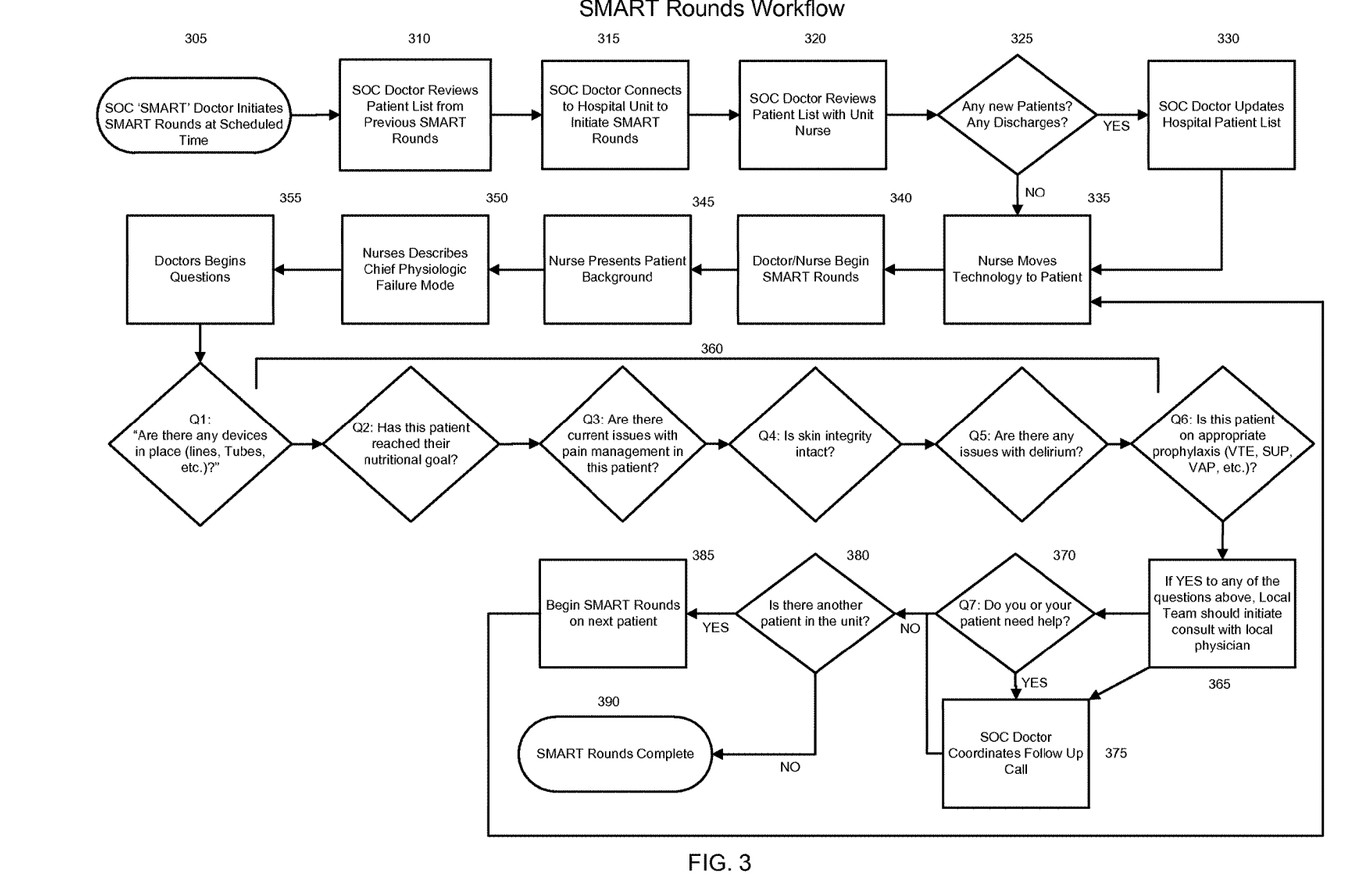
FIG. 3 is a flowchart of an evaluation workflow according to an embodiment of the invention.

FIG. 3 is a remote evaluation workflow 300 according to an embodiment of the invention. A doctor may log onto the remote evaluation system 305 via the doctor computer 120. The UI may present the doctor with a patient list and/or schedule for review 310, which may be provided by the CCC 110. The doctor and a specific care facility (e.g., a specific hospital's ICU) 315 may be connected, for example as described above with respect to FIG. 2. The doctor may review the patient list with a nurse at the facility 320. If there are new patients or discharges 325, the patient list may be updated 330. If there are no changes to the patient roster 325, the nurse may move the camera unit 131 to a first patient 335.

The remote evaluation session for the first patient may begin 340. As discussed above, the doctor may be provided with a video feed of the patient. Similarly, a camera 758 at the doctor computer 120 and a display 870 at the camera unit 131 may provide a video feed of the doctor to the patient and/or nurse in some embodiments. In the session, the nurse may present the patient's background 345 and chief physiologic failure mode 350 to the doctor, for example. The doctor may ask questions 355. For example, in an ICU setting, questions 360 may include whether there are any devices (e.g., lines, tubes, etc.) in place, whether the patient has met nutritional goals, whether there are any pain management issues, whether skin integrity is intact, whether there are issues with delirium, and/or whether the patient is on appropriate prophylaxis (e.g., venous thromboembolism, stress ulcer, ventilator-associated pneumonia, etc.). The doctor may ask questions of the nurse and may or may not interact with the patient. Of course, the system may be used in any setting for any clinical specialty.

Once the questions are asked and answered, immediate issues may be identified, and a consult with a local physician may be ordered 365. For example, in the ICU setting, if any urgent issues are identified through doctor questioning, the nurse may initiate a consult with a local physician and/or the doctor may coordinate a follow-up call, for example a remote consultation with a specialist 375. The doctor may also ask if the on-site personnel (e.g., the nurse) or the patient needs help 320. If so, the doctor may coordinate a follow-up call 375. The follow-up call may be coordinated through the doctor's computer 120 UI module 780. For example, the doctor may be able to indicate that follow-up is needed, and this information may be transmitted to the CCC 110 scheduling module 650. The CCC 110 scheduling module 650 may automatically search a listing of specialists in the memory 630 for available specialists to handle the follow-up and assign and notify one of the specialists, may automatically contact the hospital 130 to suggest the follow-up, and/or may direct call center personnel to coordinate the follow-up manually. Through this process, the doctor may provide care management by exception (e.g., the doctor may identify problems that need additional attention, and may not necessarily perform a thorough rounding examination on each patient). Management by exception may allow the remote evaluation sessions to be relatively brief, but may allow patient care to be escalated by remote and/or local follow-up if necessary. Thus, significantly fewer doctor computers 120 than hospitals 130 may be able to interact with the CCC 110 at any given time while still providing coverage of all hospitals 130.

If there are more patients to visit 380, a remote evaluation session for the next patient may begin 385. This session may proceed as described above in 335-375. If there are no more patients, remote evaluation may be completed for this location 390. As described above, the CCC 110 may receive indication of completion and/or session results. The doctor may log off or remotely visit a different location for another remote evaluation session.

Figure 4A:
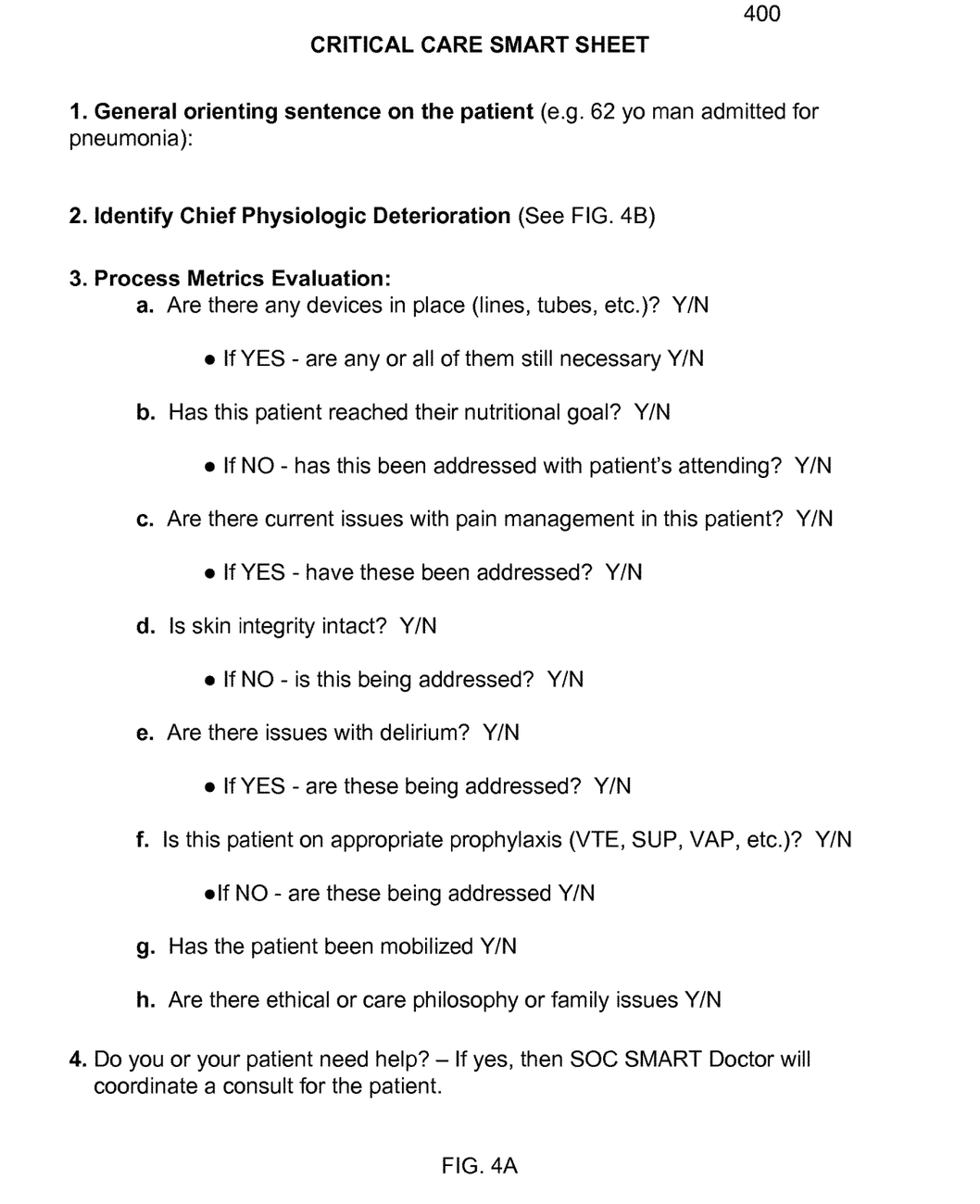
FIGS. 4A and 4B are an example of a data sheet (both sides) according to an embodiment of the invention.
Figure 4B:
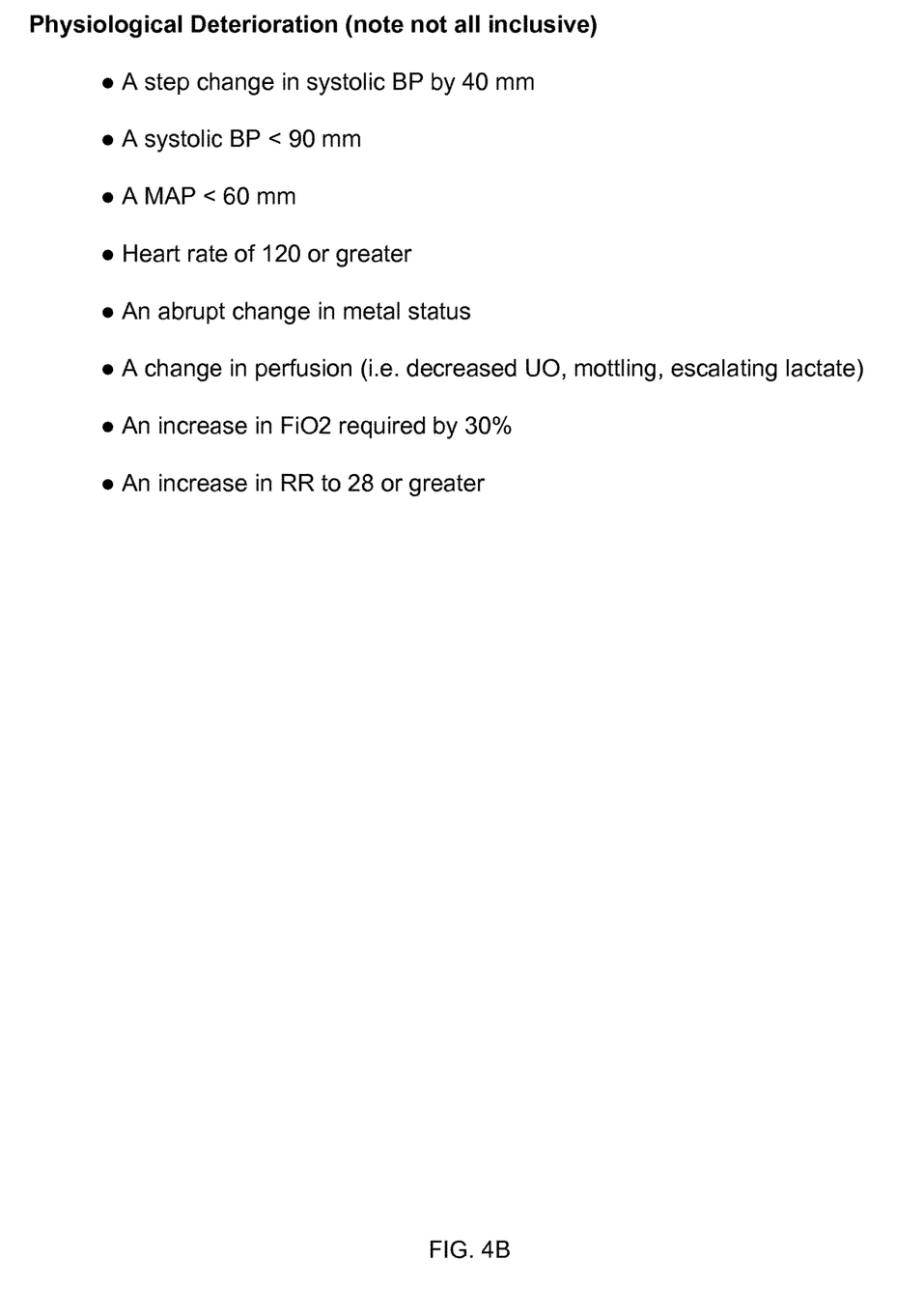

The background information and answers to questions may be used to generate a data sheet for each patient. FIGS. 4A and 4B are opposite sides of a data sheet 400 ("intensive care smart sheet" in this example) according to an embodiment of the invention. Although FIGS. 4A and 4B are directed to intensive care, this system may be employed for any clinical specialty by changing to an appropriate SMARTsheet. As shown in FIG. 4A, the data sheet 400 may enable the doctor and/or nurse to enter information generated by the remote evaluation session. The data sheet 400 may be placed in the patient's chart for use by local medical personnel and/or for comparison with past and/or future remote evaluation sessions for the patient. The data sheet 400 may be used as a template for gathering information for storage by the data module 670 into the memory 630 of the CCC 110. For example, the doctor may fill in data sheet 400 fields in the doctor computer 120 UI, and the doctor computer 120 may send the data to the CCC 110. The nurse or another individual at the hospital 130 may fill in data sheet 400 fields in a hospital 130 computer, and the hospital 130 computer may send the data to the CCC 110 data module 670. The nurse or another individual at the hospital 130 may fill in a physical data sheet and fax it to the CCC 110. The CCC 110 data module 670 may gather the information from the faxed data sheet automatically (e.g., by optical character recognition or some other method) or via manual entry into a CCC 110 computer via an input device interaction with the UI module 680.

Figure 9:
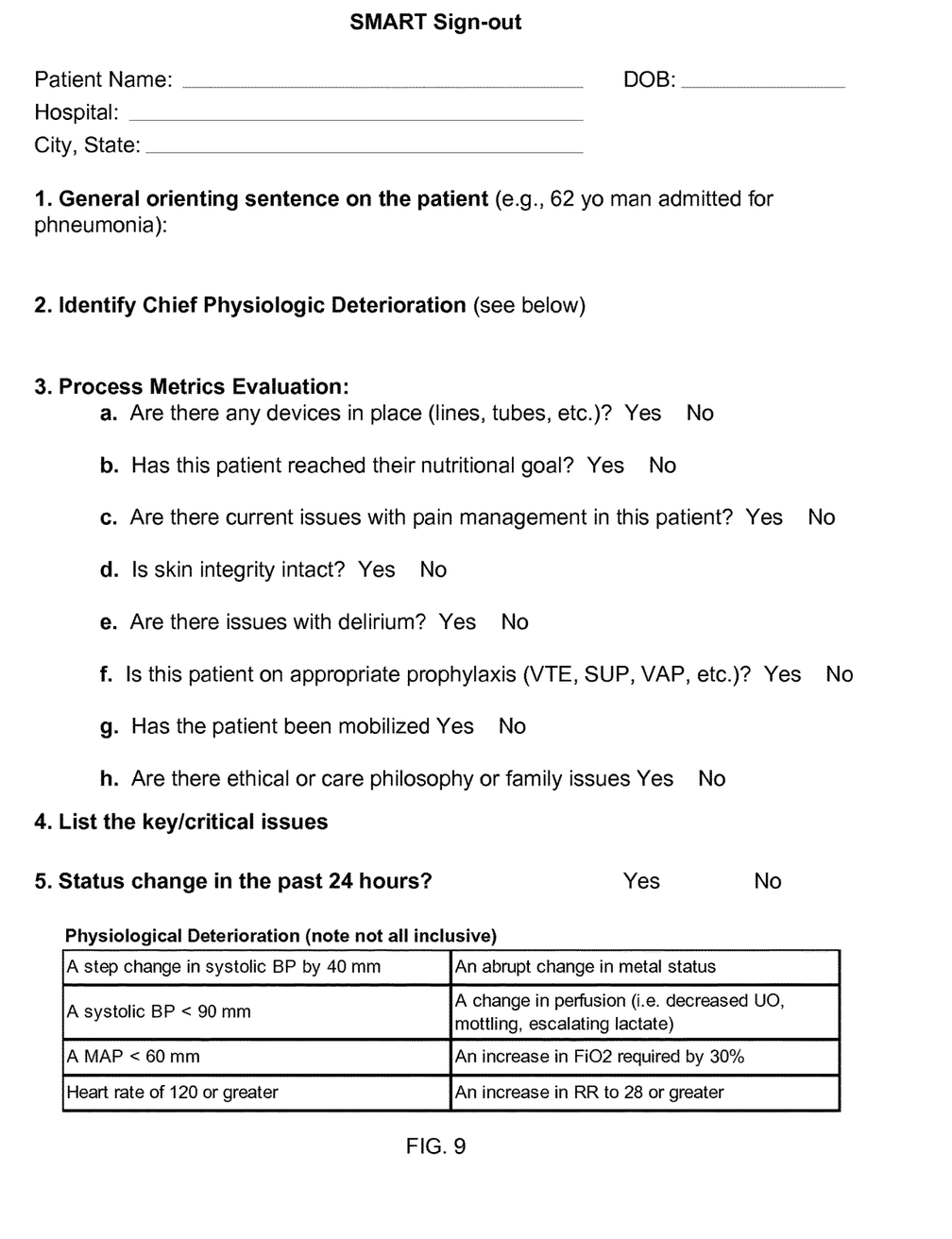
FIG. 9 is an example of a sign-out sheet according to an embodiment of the invention.

FIG. 9 shows a SMART sign out sheet that may be used at the end of a shift of a health care professional (e.g., physicians, nurses, assistants, etc.) local to the patient. This allows the health care professional to document the patients that they are responsible for and transmit this data to the CCC 110 for the next shift.

The data sent back to the CCC 110 (including data from the SMARTsheet (FIGS. 4A and 4B) and SMART sign out sheet (FIG. 9) may be used to help identify meta-trends. For example, the data may be used to identify common physiologic failure modes (see FIG. 4B), common failure points in process, common breakdowns in process metrics, which patients or situations require the most help, etc. In performing remote evaluations, data collected as described above may reveal trends applicable to individual hospitals. If a hospital has consistent issues (e.g., devices inappropriately left in place, prophylaxis problems, etc.), these may be identified if they are frequently reported by remote doctors. In another example, the data may reveal that a hospital's staff consistently does not ask for help, but remote doctors frequently identify a need for further help. As a result, hospital troubleshooting may be performed and hospital efficiency/effectiveness may be improved. This ongoing documentation may also be used in facilities/programs with metrics for quality/safety/Joint Commission standards. In an individual patient example, a patient's records accrued over multiple remote evaluation sessions may be compiled in the CCC 110 database and may be viewed, for example via the UI of the doctor computer 120. When a doctor is performing a remote evaluation session involving the patient, the doctor may be able to use trends found in the patient's past data to evaluate whether an observation of the patient represents a problem that should be flagged for follow-up or is merely indicative of the patient's base condition. Such data may be employed as a research tool to assess various metric and to suggest new ways to potentially affect the treatment of patients and quality of patient care.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

In addition, the terms "comprising", "including", etc. signify "including, but not limited to" in the specification, claims and drawings.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A method comprising:
   scheduling, with a scheduling module executed by a processor of a consult coordination center (CCC) computer comprising the processor and a database, a patient assessment session for a facility, the patient assessment session comprising an assessment of at least one patient in the facility by a remote health care professional to determine whether the at least one patient should be given more immediate care;
   assigning, with an assignment module executed by the processor, the scheduled patient assessment session to a health care professional computer;
   creating, with a connection module executed by the processor, a remote connection between the health care professional computer and a computer at the facility via a network to facilitate the patient assessment session, the remote connection comprising a video feed from the computer at the facility to the health care professional computer, the creating comprising:
      establishing, with the connection module, the remote connection; and
      handing off, with the connection module, the remote connection to the health care professional computer and the computer at the facility so that data exchanged between the health care professional computer and the computer at the facility does not pass through the CCC computer;
   monitoring, with the connection module, integrity of the remote connection during the patient assessment session after the handing off;
   retrieving, with a data module executed by the processor, a report of a previous patient assessment session at the facility from the database;
   sending, with the data module, the report of the previous patient assessment session at the facility to the health care professional computer;
   receiving, with the data module, a report of the patient assessment session; and
   storing, with the data module, the report of the patient assessment session in the database.

2. The method of claim 1, wherein:
   the scheduling comprises:
      receiving, with the scheduling module, a start time for the patient assessment session from the facility;
      determining, with the scheduling module, an approximate duration for the patient assessment session; and
      identifying, with the scheduling module, a health care professional computer associated with a health care professional who is available at the start time for the approximate duration; and
   the assigning comprises assigning, with the assignment module, the facility to the health care professional computer associated with the available health care professional.

3. The method of claim 1, wherein:
the scheduling comprises:
receiving, with the scheduling module, a start time for the patient assessment session from the facility; and
receiving, with the scheduling module, an indication of readiness from the health care professional computer coinciding with the start time; and
the assigning comprises assigning, with the assignment module, the facility to the health care professional computer in response to the indication of readiness.

4. The method of claim 1, wherein the assigning is based on a record indicating that the health care professional computer has been connected to the facility for the previous patient assessment session.

5. The method of claim 1, further comprising reestablishing, with the connection module, the remote connection when the remote connection is broken, the reestablishing comprising handing off, with the connection module, the reestablished remote connection to the health care professional computer and the computer at the facility so that data exchanged between the health care professional computer and the computer at the facility does not pass through the CCC computer.

6. The method of claim 1, wherein the report of the patient assessment session is received by the data module from:
the health care professional computer,
the computer at the facility,
via a user interface at the CCC computer,
by scanning a physical document, or
a combination thereof.

7. The method of claim 1, wherein:
the computer at the facility is coupled to a video camera at the facility; and
the computer at the facility is configured to send video captured by the video camera to the health care professional computer.

8. The method of claim 1, wherein:
the health care professional computer is coupled to a video camera; and
the health care professional computer is configured to send video captured by the video camera to the computer at the facility.

9. The method of claim 1, wherein receiving the report comprises receiving, with the data module, an indication that at least one patient in the facility requires follow-up.

10. The method of claim 9, further comprising scheduling, with the scheduling module, a follow-up session for the at least one patient requiring follow-up.

11. A consult coordination center (CCC) computer comprising:
a database;
a processor;
a scheduling module executed by the processor configured to schedule a patient assessment session for a facility, the patient assessment session comprising an assessment of at least one patient in the facility by a remote health care professional to determine whether the at least one patient should be given more immediate care;
an assignment module executed by the processor configured to assign the scheduled patient assessment session to a health care professional computer;
a connection module executed by the processor configured to:
create a remote connection between the health care professional computer and a computer at the facility via a network to facilitate the patient assessment session, the remote connection comprising a video feed from the computer at the facility to the health care professional computer, the creating comprising:
establishing, with the connection module, the remote connection; and
handing off, with the connection module, the remote connection to the health care professional computer and the computer at the facility so that data exchanged between the health care professional computer and the computer at the facility does not pass through the CCC computer; and
monitor integrity of the remote connection during the patient assessment session after the handing off; and
a data module executed by the processor configured to:
retrieve a report of a previous patient assessment session at the facility from the database;
send the report of the previous patient assessment session at the facility to the health care professional computer;
receive a report of the patient assessment session; and
store the report of the patient assessment session in the database.

12. The CCC computer of claim 11, wherein:
the scheduling module is configured to schedule the patient assessment session by:
receiving a start time for the patient assessment session from the facility;
determining an approximate duration for the patient assessment session; and
identifying, a health care professional computer associated with a health care professional who is available at the start time for the approximate duration; and
the assigning module is configured to assign the scheduled patient assessment session by assigning the facility to the health care professional computer associated with the available health care professional.

13. The CCC computer of claim 11, wherein:
the scheduling module is configured to schedule the patient assessment session by:
receiving a start time for the patient assessment session from the facility; and
receiving an indication of readiness from the health care professional computer coinciding with the start time; and
the assigning module is configured to assign the scheduled patient assessment session by assigning the facility to the health care professional computer in response to the indication of readiness.

14. The CCC computer of claim 11, wherein the assigning is based on a record indicating that the health care professional computer has been connected to the facility for the previous patient assessment session.

15. The CCC computer of claim 11, wherein the connection module is further configured to reestablish the remote connection when the remote connection is broken, the reestablishing comprising handing off the reestablished remote connection to the health care professional computer and the computer at the facility so that data exchanged between the health care professional computer and the computer at the facility does not pass through the CCC computer.

16. The CCC computer of claim 11, wherein the report of the patient assessment session is received by the data module from:

the health care professional computer,
the computer at the facility,
via a user interface at the CCC computer,
by scanning a physical document, or
a combination thereof.

17. The CCC computer of claim 11, wherein:
the computer at the facility is coupled to a video camera at the facility; and
the computer at the facility is configured to send video captured by the video camera to the health care professional computer.

18. The CCC computer of claim 11, wherein:
the health care professional computer is coupled to a video camera; and
the health care professional computer is configured to send video captured by the video camera to the computer at the facility.

19. The CCC computer of claim 11, wherein receiving the report comprises receiving, with the data module, an indication that at least one patient in the facility requires follow-up.

20. The CCC computer of claim 19, wherein the scheduling module is further configured to schedule a follow-up session for the at least one patient requiring follow-up.

21. A system comprising:
a health care professional computer;
a computer at a facility;
a consult coordination center (CCC) computer in communication with the health care professional computer and the computer at the facility via a network, the CCC computer comprising:
a database;
a processor;
a scheduling module executed by the processor configured to schedule a patient assessment session for the facility, the patient assessment session comprising an assessment of at least one patient in the facility by a remote health care professional to determine whether the at least one patient should be given more immediate care;
an assignment module executed by the processor configured to assign the scheduled patient assessment session to the health care professional computer;
a connection module executed by the processor configured to:
create a remote connection between the health care professional computer and the computer at the facility via the network to facilitate the patient assessment session, the remote connection comprising a video feed from the computer at the facility to the health care professional computer, the creating comprising:
establishing, with the connection module, the remote connection; and
handing off, with the connection module, the remote connection to the health care professional computer and the computer at the facility so that data exchanged between the health care professional computer and the computer at the facility does not pass through the CCC computer; and
monitor integrity of the remote connection during the patient assessment session after the handing off; and
a data module executed by the processor configured to:
retrieve a report of a previous patient assessment session at the facility from the database;
send the report of the previous patient assessment session at the facility to the health care professional computer;
receive a report of the patient assessment session; and
store the report of the patient assessment session in the database.

22. The system of claim 21, wherein:
the scheduling module is configured to schedule the patient assessment session by:
receiving a start time for the patient assessment session from the facility;
determining an approximate duration for the patient assessment session; and
identifying, a health care professional computer associated with a health care professional who is available at the start time for the approximate duration; and
the assigning module is configured to assign the scheduled patient assessment session by assigning the facility to the health care professional computer associated with the available health care professional.

23. The system of claim 21, wherein:
the scheduling module is configured to schedule the patient assessment session by:
receiving a start time for the patient assessment session from the facility; and
receiving an indication of readiness from the health care professional computer coinciding with the start time; and
the assigning module is configured to assign the scheduled patient assessment session by assigning the facility to the health care professional computer in response to the indication of readiness.

24. The system of claim 21, wherein the assigning is based on a record indicating that the health care professional computer has been connected to the facility for the previous patient assessment session.

25. The system of claim 21, wherein the connection module is further configured to reestablish the remote connection when the remote connection is broken, the reestablishing comprising handing off the reestablished remote connection to the health care professional computer and the computer at the facility so that data exchanged between the health care professional computer and the computer at the facility does not pass through the CCC computer.

26. The system of claim 21, wherein the report of the patient assessment session is received by the data module from:
the health care professional computer,
the computer at the facility,
via a user interface at the CCC computer,
by scanning a physical document, or
a combination thereof.

27. The system of claim 21, wherein:
the computer at the facility is coupled to a video camera at the facility; and
the computer at the facility is configured to send video captured by the video camera to the health care professional computer.

28. The system of claim 21, wherein:
the health care professional computer is coupled to a video camera; and
the health care professional computer is configured to send video captured by the video camera to the computer at the facility.

29. The system of claim 21, wherein receiving the report comprises receiving, with the data module, an indication that at least one patient in the facility requires follow-up.

30. The system of claim 29, wherein the scheduling module is further configured to schedule a follow-up session for the at least one patient requiring follow-up.

* * * * *